United States Patent
Joo et al.

(10) Patent No.: US 9,267,220 B2
(45) Date of Patent: Feb. 23, 2016

(54) NANOFIBERS, NANOTUBES AND NANOFIBER MATS COMPRISING CRYSTALINE METAL OXIDES AND METHODS OF MAKING THE SAME

(75) Inventors: Yong L. Joo, Ithaca, NY (US); Jeanne E. Panels, Ithaca, NY (US)

(73) Assignee: Cornell University, Ithaca, NY (US)

( * ) Notice: Subject to any disclaimer, the term of this patent is extended or adjusted under 35 U.S.C. 154(b) by 444 days.

(21) Appl. No.: 11/694,435

(22) Filed: Mar. 30, 2007

(65) Prior Publication Data

US 2007/0269655 A1  Nov. 22, 2007

Related U.S. Application Data

(60) Provisional application No. 60/744,023, filed on Mar. 31, 2006.

(51) Int. Cl.
*D02G 3/00* (2006.01)
*C01B 13/14* (2006.01)
(Continued)

(52) U.S. Cl.
CPC .............. *C30B 29/605* (2013.01); *B82Y 30/00* (2013.01); *C04B 35/624* (2013.01); *C04B 35/6224* (2013.01); *C04B 35/62259* (2013.01); *C04B 35/62268* (2013.01); *C04B 35/62847* (2013.01); *C04B 35/62855* (2013.01); *C30B 5/00* (2013.01); *C30B 29/16* (2013.01); *D01D 5/0069* (2013.01); *D01F 9/08* (2013.01);
(Continued)

(58) Field of Classification Search
CPC ........ C30B 39/605; C30B 5/00; C30B 29/16; Y10T 428/2935; Y10T 428/2958; Y10T 428/2915; B82Y 30/00; C04B 35/6224; C04B 35/62259; C04B 35/62268; C04B 35/624; C04B 35/62847; C04B 35/62855; C04B 2235/3212; C04B 2235/3232; C04B 2235/3236; C04B 2235/3241; C04B 2235/3244; C04B 2235/3272; C04B 2235/3293; C04B 2235/441; C04B 2235/5264; C04B 2235/5284; C04B 2235/5409; D01D 5/0069; D01F 9/08
USPC .......................................................... 977/762
See application file for complete search history.

(56) References Cited

U.S. PATENT DOCUMENTS

2002/0035032 A1* 3/2002 Koper et al. ................... 502/201
2005/0072213 A1* 4/2005 Besnard et al. ............... 73/31.06
(Continued)

FOREIGN PATENT DOCUMENTS

JP  04187237 A  *  7/1992

OTHER PUBLICATIONS

Panels et al., "Incorporation of Vanadium Oxide in Silica Nanofiber Mats via Electrospinning and Sol-gel Synthesis," Journal of Nanomaterials. 2006, vol. 2006, No. 41327; pp. 1-10.
(Continued)

*Primary Examiner* — Jeremy R Pierce
(74) *Attorney, Agent, or Firm* — Harris Beach PLLC

(57) ABSTRACT

Inorganic nanofibers comprise an inorganic matrix material surface functionalized with at least one metal oxide in crystalline form. Crystal growth on external surfaces may occur in substantial alignment with a longitudinal axis of the nanofibers, and the crystals are typically between about 10.0 nm and 30.0 nm in size. The nanofibers may be hollow (i.e., nanotubes) or they may be randomly dispersed together in the form of a nanofiber mat. Methods for making the nanofibers comprise spinning a dispersion comprising linear polymers and metal oxide precursors.

16 Claims, 4 Drawing Sheets

(51) Int. Cl.
  *C30B 29/60* (2006.01)
  *B82Y 30/00* (2011.01)
  *C04B 35/622* (2006.01)
  *C04B 35/624* (2006.01)
  *C04B 35/628* (2006.01)
  *C30B 5/00* (2006.01)
  *C30B 29/16* (2006.01)
  *D01D 5/00* (2006.01)
  *D01F 9/08* (2006.01)

(52) U.S. Cl.
  CPC . *C04B2235/3212* (2013.01); *C04B 2235/3232* (2013.01); *C04B 2235/3236* (2013.01); *C04B 2235/3241* (2013.01); *C04B 2235/3244* (2013.01); *C04B 2235/3272* (2013.01); *C04B 2235/3293* (2013.01); *C04B 2235/441* (2013.01); *C04B 2235/5264* (2013.01); *C04B 2235/5284* (2013.01); *C04B 2235/5409* (2013.01); *Y10T 428/2915* (2015.01); *Y10T 428/2935* (2015.01); *Y10T 428/2958* (2015.01)

(56) References Cited

U.S. PATENT DOCUMENTS

2006/0226580 A1* 10/2006 Xia et al. ............... 264/465
2007/0151921 A1* 7/2007 Nakano et al. ......... 210/500.21

OTHER PUBLICATIONS

Ko et al., "Fabrication of SiO2/ZrO2 Composite Fiber Mats via Electrospinning," Journal of Porous Materials. 2006, vol. 13; pp. 325-330.

Lee et al., "Preparation of SiO2/TiO2 Composite Fibers by Sol-gel Reaction and Electrospinning," Materials Letters. 2007, vol. 61; pp. 889-893.

* cited by examiner

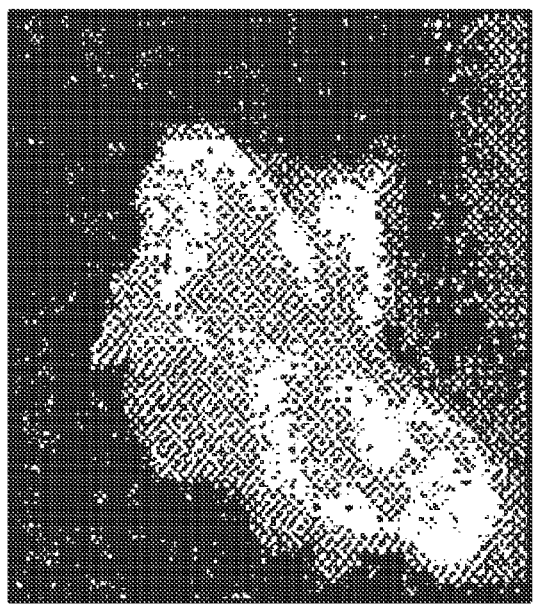 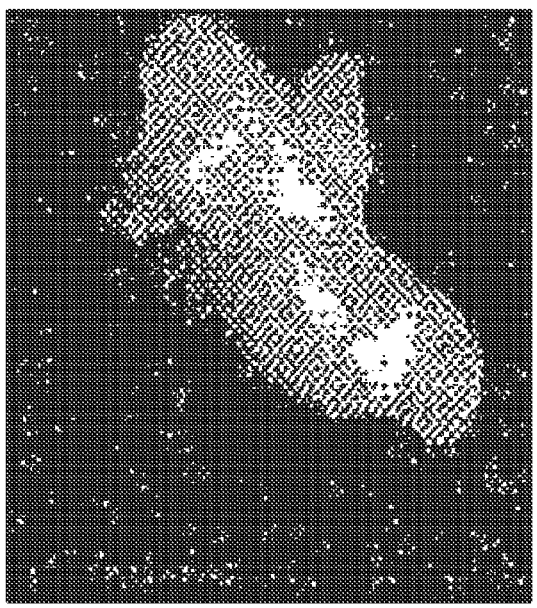
FIG. 3A  FIG. 3B
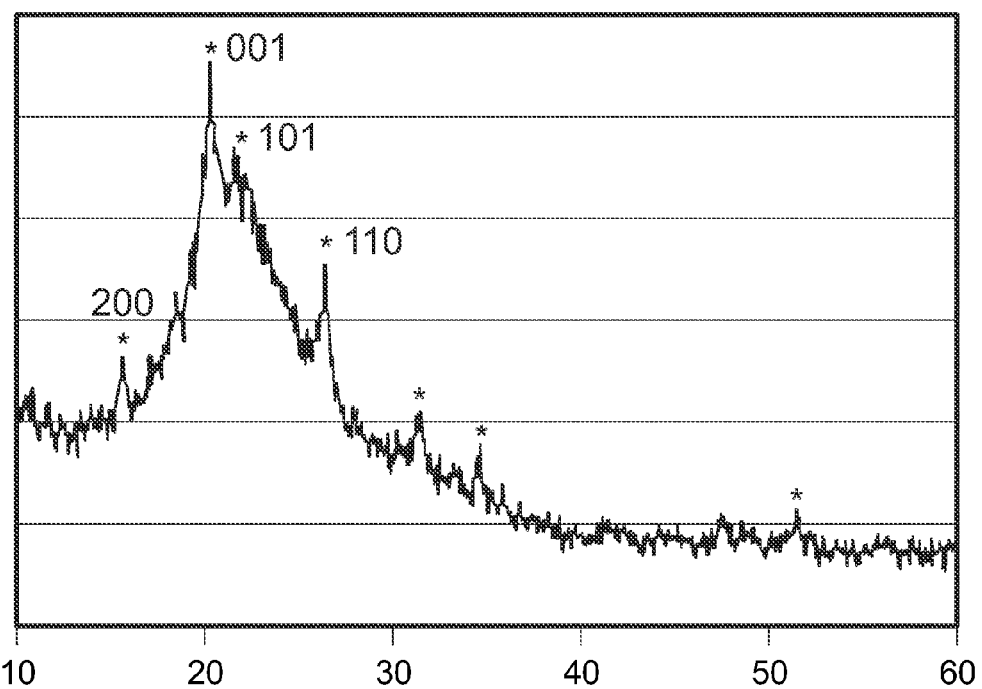
FIG. 4

NANOFIBERS, NANOTUBES AND NANOFIBER MATS COMPRISING CRYSTALINE METAL OXIDES AND METHODS OF MAKING THE SAME

PRIORITY CLAIM

The present application claims priority to U.S. Provisional Pat. App. 60/744,023, filed on Mar. 31, 2006, the contents of which are hereby incorporated by reference in their entirety.

STATEMENT OF GOVERNMENT RIGHTS

This invention was made with Government support under contract number 2004-04470, awarded by the U.S. Department of Agriculture. The government has certain rights in this invention.

FIELD OF INVENTION

The present invention relates to nanofibers and more particularly to surface-functionalized nanofibers, nanotubes and nanofiber mats as well as methods for making the same.

BACKGROUND

Nanofibers may be collected as non-woven nanofiber mats, which are useful in various applications, including sensing, filtration and the like. Typical nanofiber mats are constructed of carbon based nanofibers, which optionally comprise amorphous metal oxides. These carbon-based nanofiber mats are most often built on polyvinyl alcohol, polyvinyl acetate or polyacrylonitrile backbones.

There is a need for improved nanofibers and nanofiber mats comprising a relatively high surface to volume ratio (and thus a large number of potential active sites) along with a relatively high thermal stability.

SUMMARY OF INVENTION

In one aspect, the present invention is directed to an inorganic nanofiber, nanotube or nanofiber mat comprising an inorganic matrix material comprising an external surface and a plurality of inorganic metal oxide crystals positioned on the external surface of the inorganic matrix material. One or more of the metal oxide crystals may be positioned in substantial alignment with a longitudinal axis of the inorganic nanofiber, with between about 25% and about 50% of being typical. The metal oxide crystals may be physically entrapped on the external surface. Further, at least some of the metal oxide crystals may be oriented at an acute angle or randomly relative to the external surface. Most often, between about 8% and about 20% of the external surface comprises the metal oxide crystals. In preferred embodiments, the inorganic matrix material comprises silica or calcium phosphate, but may also comprise $V_2O_5$, $VO_2$, $TiO_2$, $Fe_2O_3$, $Fe_3O_4$, $SnO_2$, $ZrO_2$, $BaTiO_3$, $SrTiO_3$ or combinations thereof. The nanofiber is capable of withstanding high melting points, between about 1,000° C. and about 1,200° C. and may comprises a specific surface area between about 800.0 m²/g and 1,000.0 m²/g.

In another aspect, the present invention is directed to a method for making a plurality of nanofibers comprising providing a dispersion comprising at least one linear polymer, subjecting the dispersion to electrospinning and collecting the plurality of nanofibers. The linear polymer may comprise the general formula:

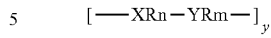

$$[\text{---XRn---YRm---}]_y$$

wherein $R_n$-$R_m$ are the same or different and independently comprise O, H, a lower alkyl group comprising $C_x$ where x=1-4 or a lower hydroxy alkyl group comprising $C_x$ where x=1-4 and where n and m range from 0 and 3, wherein X and Y are the same or different and independently comprise Ti, V, Fe, Si, Sn, Ba, Zr, Sr, Ca, O or phosphate, and y=an integer between 1 and 1,000. In an alternate embodiment, X and Y may be the same or different and independently comprise a metal, oxygen, nitrogen, selenium, sulfur, phosphorous or phosphate. The metal may be a transition metal or an alkali earth metal or any of the other above-identified metals. The linear polymer typically comprises an elongational viscosity between about 1,000 poise and 3,000 poise and a molecular weight between about 100,000 amu to about 300,000 amu.

The method may incorporate additional steps. The method may further comprise forming the dispersion through sol-gel synthesis, wherein the dispersion does not comprise a gel or a three dimensional network. The method may also incorporate a metal oxide precursor into the dispersion. Typically, the dispersion does not comprise a polymeric binder. The method may also comprise co-axial electrospinning and a calcination step after the collecting step. The calcining step is preferably carried out for about 2.0 hours to about 12.0 hours at temperatures ranging from about 500° C. to about 1,200° C. Additionally, the collected nanofibers may be exposed to deionized water prior to the calcining step.

BRIEF DESCRIPTION OF THE DRAWINGS

Certain embodiments of the present invention are illustrated by the accompanying figures. It should be understood that the figures are not necessarily to scale and that details not necessary for an understanding of the invention or that render other details difficult to perceive may be omitted. It should be understood, of course, that the invention is not necessarily limited to the particular embodiments illustrated herein.

FIG. 3A is a cross-sectional TEM image of FIG. 2A;

FIG. 3B is a cross-sectional TEM image of FIG. 2B;

FIG. 4 is an X-ray diffraction pattern of the nanofibers of the present invention after calcination, showing various crystal peaks;

DETAILED DESCRIPTION

Figure 1A:
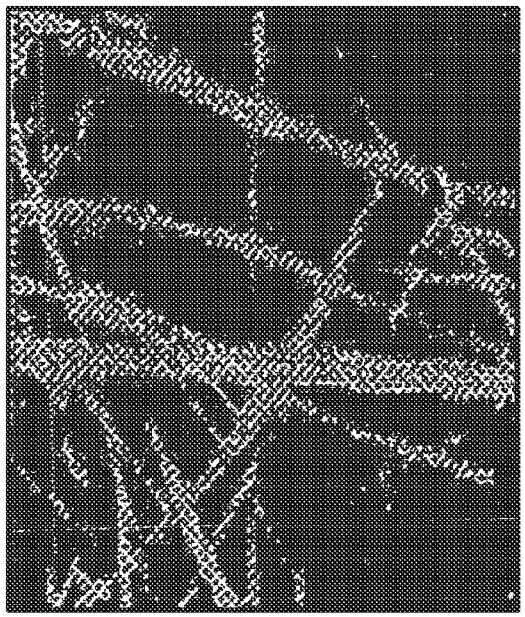
FIG. 1A is scanning electron microscope ("SEM") image of a nanofiber mat made in accordance with one embodiment of the present invention.

The nanofibers of the present invention may comprise an inorganic matrix material and at least one crystalline metal oxide, wherein a surface of the inorganic material is functionalized with the at least one crystalline metal oxide. A scanning electron microscope image of a plurality of nanofibers according to one embodiment of the present invention is shown at FIG. 1A. When the plurality of nanofibers is randomly dispersed, with at least some of the nanofibers in physical contact with one another, a non-woven nanofiber mat is formed. The nanofiber mat can be electrically conducting.

The inorganic material of the nanofibers may exhibit a three-dimensional network structure and comprise silica—$SiO_2$—though other types of inorganic materials, including calcium phosphate, may also be employed. Since inorganic materials advantageously exhibit relatively high thermal stability, the nanofibers of the present invention can be used for applications involving high temperatures, such as catalytic processing. In addition, the high melting points of these inorganic materials help prevent unwanted break-down or disintegration of the material during synthesis. The melting point of the nanofibers of the present invention may be between about 800° C. and 1,500° C., and more particularly between about 1,000° C. and 1,200° C.

The crystalline metal oxide used in the nanofibers may comprise a transition metal. By way of example but not limitation, suitable metal oxide crystals for use with the present invention include $V_2O_5$, $TiO_2$, $Fe_2O_3$, $SnO_2$, $ZrO_2$, $BaTiO_3$, $SrTiO_3$ and combinations thereof. These metal oxides may also be employed as the inorganic material itself.

Figure 2A:
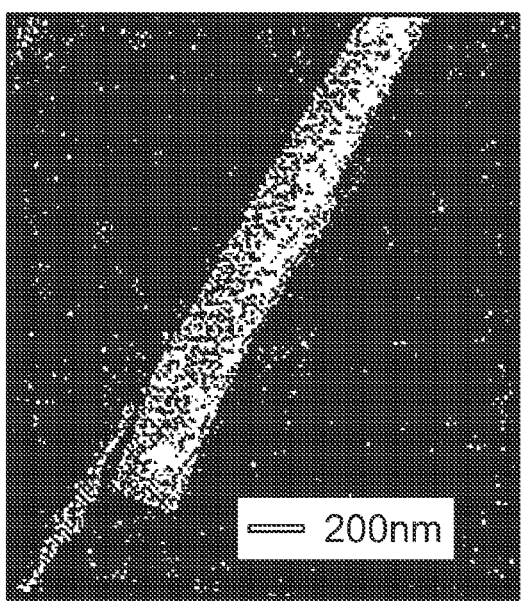
FIG. 2A is an energy filtered transmission electron microscope ("TEM") image of the nanofibers of the present invention, with vanadium filtered out.
Figure 2B:
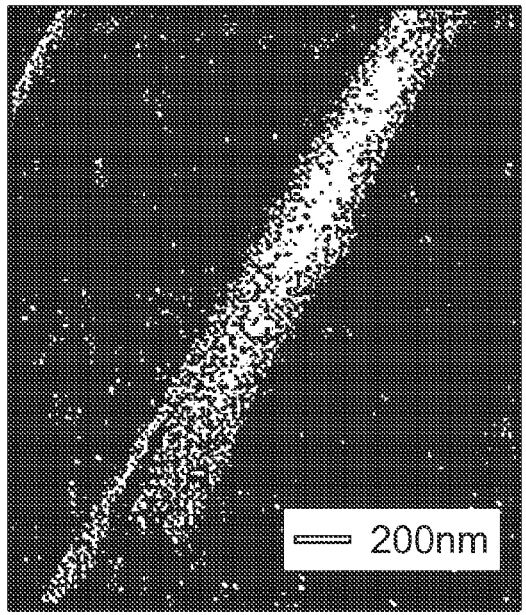
FIG. 2B is a TEM image of the nanofibers of the present invention, with silicon filtered out.

The metal oxide may be positioned within the inorganic material and/or on external surfaces thereof. When the metal oxide is exposed to oxygen it tends to crystallize. Thus, while metal oxides within the nanofiber are usually amorphous (though they may be crystalline), metal oxides on external nanofiber surfaces typically exhibit a crystalline form. In either event, the metal oxide is most often physically entrapped within the inorganic material (i.e., the metal oxide is non-covalently bonded to the inorganic material). FIGS. 2A-3B illustrate the positioning of the metal oxide, both on external surfaces of a nanofiber and internally. As shown in FIG. 2B, metal oxide crystals on external surfaces are indicated by the dark areas at opposite ends of the nanofiber. FIG. 3B, which represents a cross-sectional TEM image of a nanofiber according to one embodiment of the present invention, also indicates the presence of metal oxide in the darkened areas.

To determine the presence of metal oxide crystals on external surfaces, X-ray photoelectron spectroscopy ("XPS") may be employed. That is, the atomic ratio of transition metal to oxygen on nanofiber surfaces is determined through XPS and compared to known ratios of these elements in crystalline metal oxides. For example, the presence of vanadium pentoxide $V_2O_5$ crystals is indicated when the results of XPS confirm a ratio of vanadium to oxygen of 2:5.

The orientation and size of the metal oxide crystals may be determined through X-ray diffraction, carried out with a Theta-Theta Diffractometer available from Scintag, Incorporated. An X-ray diffraction pattern is shown in FIG. 4. Based on the various peaks, including the major peak at 001, at least some crystal growth on external surfaces occurs in substantial alignment with a longitudinal axis of the nanofibers (e.g., 25% or more and more particularly 50% or more of the external crystal growth may exhibit this configuration). Thus, a plurality of metal oxide crystals may be oriented at an acute angle relative to the external surfaces of the nanofibers, though at least some crystals are oriented randomly in a variety of directions. Given the heights and areas under the peaks, the crystals are typically between about 10.0 nm and 30.0 nm in size.

Most often, about half of the metal oxide is positioned within the material while the other half grown on the external surface. About 5% to about 20%, and in some cases between about 30% and 50% of the external surface of the inorganic material comprises the crystalline metal oxide, with about 8% to about 12%, about 15% to about 20% and more particularly about 10% being typical. The degree of coverage may be determined through chemical adsorption, using a chemisorption analyzer for example.

Figure 5:
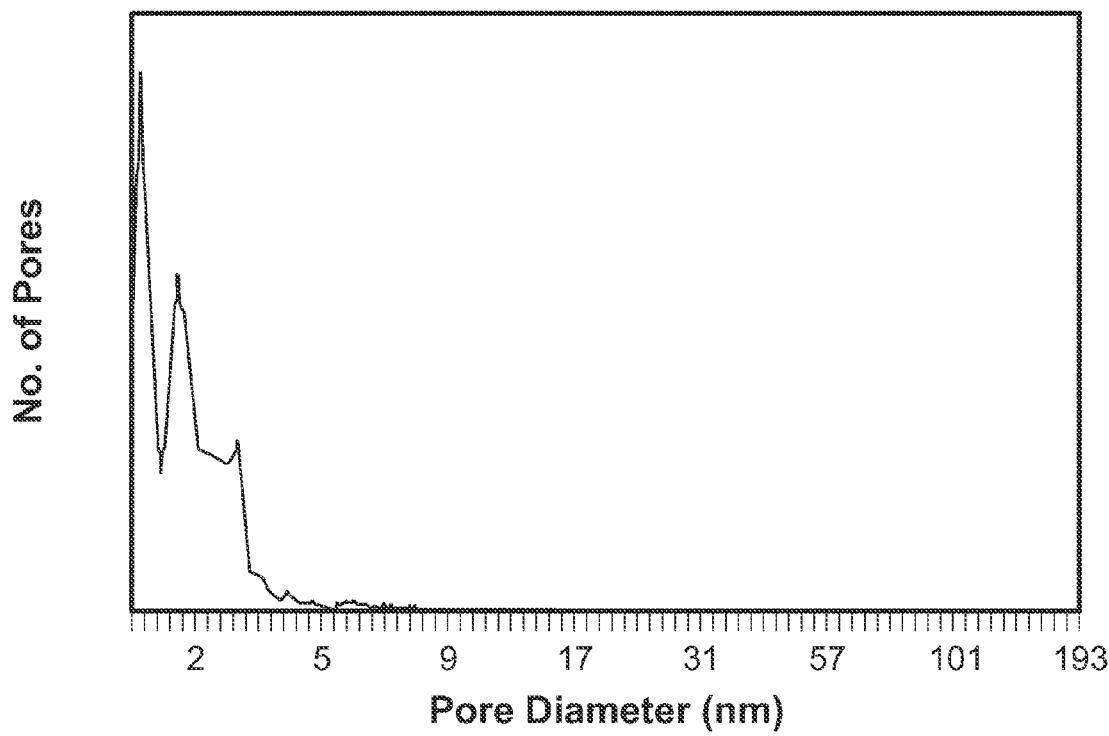
FIG. 5 is a graphical representation of pore number as a function of pore diameter for one embodiment of the nanofiber mat of the present invention.

When the nanofibers take the form of the nanofiber mat, the mat may exhibit a relatively high specific surface area, owing to relatively small nanofiber diameters and the presence of porosity within the nanofiber mat. The specific surface area of the nanofiber mat, measured with a Micrometrics Phys/Chami Sorption Analyzer, is typically greater than about 10 m2/g and more particularly between about 100 $m^2/g$ and 1,200 $m^2/g$ or 600 $m^2/g$ and 1,100 $m^2/g$ and still more particularly between about 800 $m^2/g$ and about 1,000 $m^2/g$. The inorganic nanofibers that make up the mat are relatively thin, comprising diameters between about 100.0 nm to about 500.0 nm, and more particularly between about 200.0 nm to about 400.00 nm. The total porosity of the nanofiber mat may be between about 10% and 50%, with about 20% to about 30% being typical. The pores are defined by the tiny interstices or gaps between the randomly dispersed nanofibers that form the mat as well as the internal pores within the nanofibers themselves. As shown in FIG. 5, the majority of the pores are less than 5.0 nanometers in diameter and typically exhibit diameters between about 1.0 nanometers and 3.0 nanometers.

To make the nanofibers of the present invention, a stepwise process may be employed. In one embodiment, sol-gel synthesis, with incorporation of a metal ethoxide precursor, is followed by electrospinning, optional hydrolysis and calcination.

The goal of the sol-gel synthesis is to yield a reaction product comprising a relatively high elongational viscosity, for example between about 1,000 poise to about 3,000 poise, with about 2,000 poise to about 2,500 poise being typical. To achieve the appropriate elongational viscosity, the molar ratio of inorganic material to solvent to water to catalyst may be adjusted. The reaction product of the sol-gel synthesis preferably does not comprise a three dimensional network or gel and typically comprises at least one linear polymer exhibiting the following general formula:

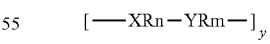

$$[-XR_n-YR_m-]_y$$

wherein $R_n$-$R_m$ are the same or different and independently comprise O, H, a lower alkyl group comprising $C_x$ where x=1-4 or a lower hydroxy alkyl group comprising $C_x$ where x=1-4 and where n and m range from 0 and 3, wherein X and Y are the same or different and independently comprise Ti, V, Fe, Si, Sn, Ba, Zr, Sr, Ca, O or phosphate, and y=an integer between 1 and 1,000. $R_n$ and $R_m$ may, for example, comprise lower alkyl groups, such as methyl, ethyl, propyl or butyl groups or lower hydroxy alkyl groups, such as hydroxy methyl, ethyl, propyl or butyl groups. In an alternate embodiment, X and Y may be the same or different and independently comprise a metal, oxygen, nitrogen, selenium, sulfur, phosphorous or phosphate. The metal may be a transition metal or an alkali earth metal or any of the other above-identified metals. The molecular weight of the linear polymer is typically between about 10,000 amu and 300,000 amu and more particularly between about 100,000 amu to 200,000 amu.

Such a configuration helps optimize nanofiber formation during the electrospinning step, avoiding unwanted breakdown or disintegration of material. The control of elongational viscosity in electrospinning is more important than in conventional spinning because of higher elongational deformation during electrospinning.

A sol-gel synthesis reaction using tetraethyl orthosilicate ("TEOS") as the inorganic precursor and vanadium oxytri-isopropoxide ("VOTIP") as the metal oxide precursor serves as an illustrative example. TEOS is added to a solvent of ethanol and water, followed by the dropwise addition of a catalyst, comprising a solution of water and hydrochloric acid, with vigorous stirring. The overall molar ratio of TEOS: EtOH: H20:HCL is 1:2:2:0.01. A solution of VOTIP and ethanol is added until the overall solution comprises 20 mol % vanadium. Although polymeric organic binders; such as polyvinyl alcohol may be employed, the reaction may proceed without the use of such binders. The solution is heated for one to three hours at a temperature of about 50° C. Following these steps yields a dispersion comprising at least one linear chain with the general formula:

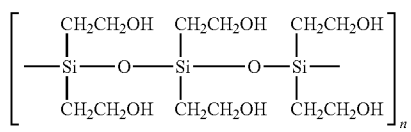

wherein n=an integer between 1 and 100. VOTIP is typically suspended within the dispersion.

The foregoing reaction conditions may vary if other inorganic materials or metal precursors are employed. The common goal, however, should be recovery of a reaction product comprising an elongational viscosity between about 1,000 poise to about 3,000 poise, followed by electrospinning and calcination.

If calcium phosphate is used as the inorganic material, the following reaction conditions may be employed. In particular, triethyl phosphate is added to anhydrous ethanol in a vial. Distilled water is added and the solution is allowed to hydrolyze for about 1.0 hour with vigorous stirring. Calcium nitrate tetrahydrate dissolved in anhydrous ethanol is added dropwise to the triethyl phosphate solution while stirring. The molar rations of Ca:P:water:ethanol was about 1.67:1:3-6.5: 7.4-14.8. This solution is aged for about 16.0 hours. After aging, the solvents are evaporated at 80° C. for about 6.0 hours to obtain a clear viscous liquid. A solution of 10% by weight polyvinyl alcohol and water is mixed with the calcium phosphate solution in a volumetric ratio of 9:1 or 8:2. After evaporation of solvents at 80° C., the calcium phosphate sol is stirred for about an hour to obtain a relatively homogeneous mixture.

The procedure for the sol-gel synthesis of calcium phosphate may proceed by the following reaction:

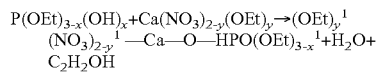

During the time the sol is left to age, the hydrolyzed phosphorus sol (which may be in the form of phosphoric ester $P(OEt)_{3-x}(OH)_x$) interacts with the calcium sol in the form of $Ca(NO_3)_{2-y}(OEt)_y$ in anhydrous ethanol and $Ca^{2+}$ in water to form oligomeric derivatives containing Ca—O—P bonds.

If titanium dioxide is used as the inorganic material, a solution that undergoes a sol-gel synthesis reaction may be prepared with the molar ratio of titanium isopropoxide:isopropanol:acetic acid being 1:2:2.5. After vigorous mixing to produce a homogenious solution, the solution is places in a 70° C. oven to accelerate the sol-gel transition. After ripening for about 0.5 hours to about 1 hour the solution is removed from the oven.

Various metal oxide precursors may also be utilized. If titanium isopropoxide is employed as the metal precursor, for example, the molar ratio of inorganic material to solvent to water to catalyst may be adjusted to between about 0.5 to 1:1:1:0.01, with addition of titanium isopropoxide at 50 mol % in the overall solution and heating for about 0.5 hours at between about 70° C. and 80° C. If zirconium acetate is employed, the molar ratio may be 0.8 to 1:1:1:0.01, with addition at 20 mol % and heating for about 0.5 hours at between about 70° C. and 80° C. If iron nitrate is employed, the molar ratio may be 1:1:2:0.01, with addition at 25 mol % and heating for about 12.0 hours at 30° C. Finally, if dibutyltin diacetate or tin tert-butoxide is employed, the molar ratio may be 1:2:2:.0.01, with addition at 20 mol % and heating for about 0.5 hours at 50° C.

After formation of the dispersion comprising linear chains and suspended metal precursor, the dispersion is subjected to electrospinning. Electrospinning is a fiber formation process that relies on electrical, rather than mechanical forces to form thin fibers with diameters ranging between about 100 nm and about 10.0 microns. A strong electric field is used to draw a solution from the tip of a capillary to a grounded collector. The electric field causes a pendant droplet of the solution at the capillary tip to deform into a conical shape. When the electrical force at the surface of the tip overcomes the surface tension of the solution, a charged jet is ejected. The jet moves toward the collector plate, which acts as a counter electrode. The solvent begins to evaporate after jet formation, causing the deposit of a thin fiber on the collector. To the extent solvent remains, the fibers may be heated to about 150° C. to remove residual solvent.

Figure 6:
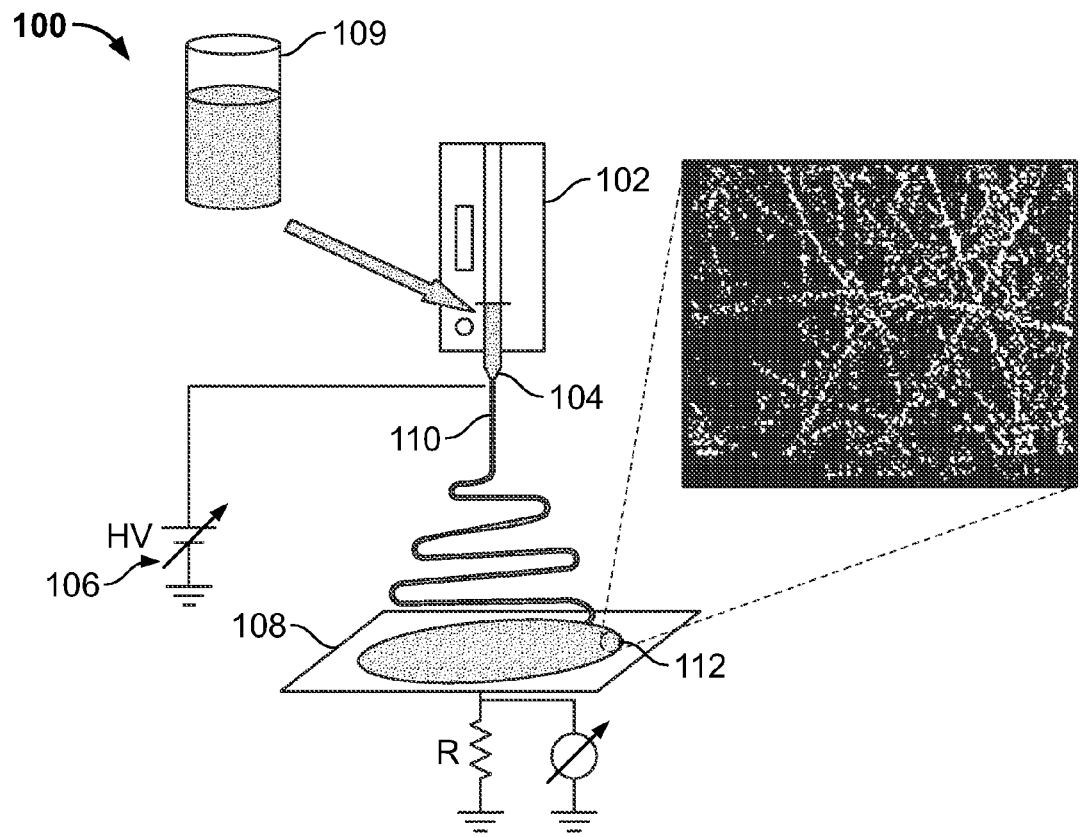
FIG. 6 is a perspective view of an electrospinning apparatus used to prepare the nanofibers of the present invention.

Referring now to FIG. 6, one embodiment of an electrospinning apparatus 100 for use with the present invention is illustrated. Apparatus 100 comprises syringe 102, comprising an inner diameter of between about 0.20 millimeters to about 0.60 millimeters, tip 104, high voltage supplier 106 positioned at or near tip 104, and collection plat 108, constructed of a conductive material, such as aluminum, stainless steel or a surface oxidized silicon. The diameter of nanofibers may be decreased by decreasing the inner diameter of syringe 102. The distance between tip 104 and collector 108 is about 10.5 centimeters. High voltage supplier 106 includes a voltage of about 20 kV. Collector 108 is grounded to create an electric field difference between tip 104 and collector 108, causing jet 110 to move from the high electric field at tip 104, to grounded collector 108.

Once apparatus 100 is assembled, dispersion 109 created during the sol-gel synthesis step is placed into syringe 102, and pumped therethrough at a relatively constant flow rate of about 0.03 milliliters per minute. As pumping continues, charged jet 110 is ejected and elongates as it moves towards collector 108. Thus, a plurality of randomly oriented nonwoven ultra-thin fibers or nanofibers 112 are collected on collector 108. At this point, the nanofibers 112 comprise a three-dimensional silica network, with amorphous vanadium dispersed throughout.

Figure 7:
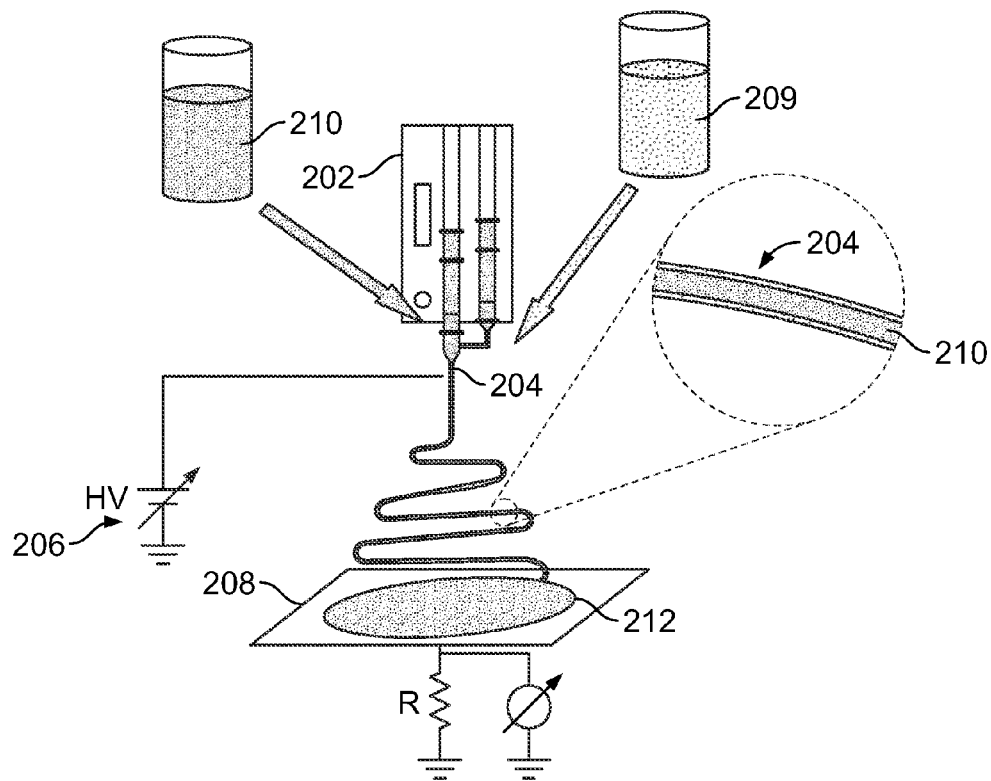
FIG. 7 is a perspective view of an alternate set-up of the electrospinning apparatus of FIG. 6.

In an alternate embodiment, shown in FIG. 7, co-axial electrospinning may be employed. Co-axial electrospinning typically yields a greater percentage of metal oxide crystals on the external surface of the collected nanofibers than traditional electrospinning. Specifically, about 15% to about 20% of the external surface of the inorganic material may comprise a crystalline metal oxide after calcination, while between about 8% and 12% is typical for non-co-axial electrospinning.

Co-axial electrospinning apparatus 200 comprises dual syringe 202 which comprises an internal tube positioned within an external tube, tip 204, high voltage supplier 206 and collector 208 for receiving nanofibers 212. Under this construction, an internal jet within an external jet is ejected from the syringe; the internal jet may comprise organic substances, such as mineral oil 210, while the external jet comprises dispersion 209, prepared during sol-gel synthesis. When mineral oil 210 is used, hollow nanofibers or nanotubes are present after the calcination step discussed below.

Alternatively, the sol-gel dispersion may be subjected to conventional mechanical spinning using an extruder, die and winder. Conventional spinning employs a mechanical force to draw fibers out of solution and yields fiber diameters between about 3.0 microns and about 5.0 microns.

After collection of the nanofibers, they are subjected to calcination. Calcination involves heating to relatively high temperatures. The calcination temperature and time depend upon the materials being used as well as the needs of the user. The typical temperature ranges from 500° C. to about 1,200° C. and more particularly from about 600° C. to about 800° C. Calcination is typically carried out anywhere between two and twelve hours and more particularly between about five to seven hours.

Calcination impacts several properties of the nanofiber mat. Calcination decreases nanofiber diameters and internal porosity and transforms amorphous metal oxides into crystals.

Figure 1B:
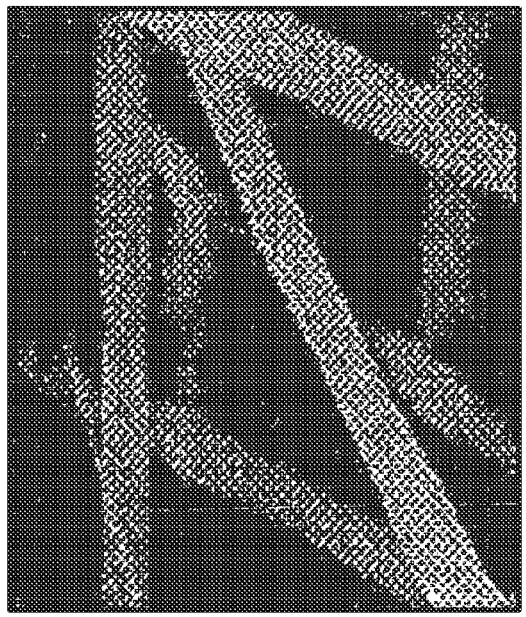
FIG. 1B is an SEM image of the nanofiber mat of FIG. 1A, prior to the calcination step.

SEM images, at FIGS. 1A and 1B, demonstrate that the average diameter of nanofibers made in accordance with the present invention decreases after calcination. FIG. 1A shows the nanofibers after calcination while FIG. 1B shows them before. Higher temperatures produce nanofibers with smaller diameters.

In addition, calcination typically decreases and ultimately removes the internal porosity of the inorganic material. Thus, provided calcination does not proceed too far, the inorganic material may comprise a plurality of pores. At least one of which exhibits a diameter between 0.1 nm and about 10.0 nm and more particularly between about 2.0 nm and about 5.0 nm.

Figure 8:
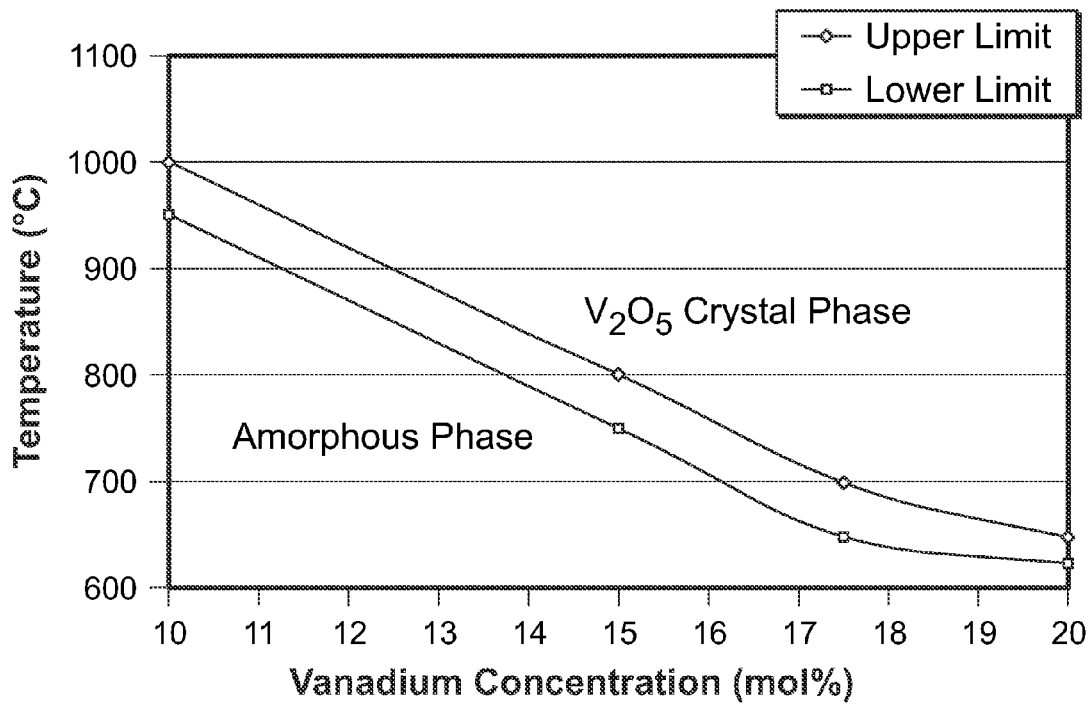
FIG. 8 is a phase diagram for the nanofibers of the present invention.

X-ray diffraction patterns obtained after calcination indicate the presence of orthorhombic vanadium pentoxide crystals $V_2O_5$. A phase diagram based on these X-ray diffraction patters is shown at FIG. 8. The lower limit temperature line represents the first sign of the nucleation of $V_2O_5$ crystals, while the upper limit temperature line represents the onset of the formation of well-defined $V_2O_5$ crystal peaks. Calcination above the lower limit temperature limit typically results in the formation of $V_2O_5$ crystals, with the degree of crystallization dependent upon both calcination time and temperature. FIG. 8 also illustrates crystallization as a function of temperature and metal concentration. It bears noting that the onset temperature for phase transition to crystalline $V_2O_5$ decreases with increasing vanadium contents. Similarly, conductivity of the reaction product of the sol-gel synthesis also decreases with increasing vanadium contents.

The final product generated by the above-described three step process is a nanofiber mat comprising a plurality of silica-bases nanofibers. Some nanofibers within the mat may be adhered to one another, based on the presence of residual solvent. The silica-based nanofibers may comprise a three-dimensional silica-based network and vanadium pentoxide crystals positioned on external surfaces thereof, though some crystals may reside completely within the silica-based material. To increase crystal content on external surfaces, the fibers may be places in deionized water for 0.5 hours to about 1 hour prior to calcination. This step drives a hydrolysis reaction, which ultimately increases crystal growth by between about 15% to about 50% of the original coverage (e.g., crystal coverage of external surfaces increases from 8% to 12%)

Depending on the composition of the nanofibers and the metal oxide crystals associated therewith, the present invention may be used in a variety of different ways, including, without limitation, in sensing, filtering and catalytic applications.

For instance, silica-based nanofiber mats comprising vanadium pentoxide crystals may be used to sense the presence of toxic or flammable gases, such as ammonia or hydrocarbons in a conventional gas flow apparatus. With the nanofiber mat deposited on a surface oxidized silicon substrate, the presence of even trace amounts of these gases can be detected by measuring the resistance variation as the transition metal is reduced to oxidized. The resistance of nanofiber mats at various concentrations of gases and flow rates can be readily measured by a multimeter system with a high input impedance. Sensing in this manner effectively utilizes the entire surface area of the nanofibers as the gases can flow throughout the nanofiber network, contacting crystals on the external surfaces of a plurality of nanofibers.

Nanofibers comprising other metal oxides are also useful. When iron oxides are employed, the nanofiber mat may be used to transform harmful gases, such as carbon monoxide and nitrous monoxide into their harmless counterparts—carbon and nitrous dioxide respectively. Nanofibers comprising titanium oxides can be used as filtering agents to deodorize, clean and sterilize, as the presence of light triggers reactions that kill organic biomolecules.

When calcium phosphate is employed as the inorganic material, the nanofiber mat may be used for bone and dental tissue regeneration. For example, calcium phosphate nanofiber mats may be electrospun on the surface of a soft tendon tissue so that the tendon can be directly connect with hard bone to reconstruct an injured ligament.

EXAMPLES 1(a-b)

The present invention is further illustrated by the following examples which, however, are not intended to limit the same.

Example 1(a)

To produce silica nanofibers, a solution that undergoes a sol-gel synthesis reaction was prepared with the molar ratio of TEOS:EtOH:$H_2O$:HCl being 1:2:2:0.01. After vigorous mixing to produce a homogeneous solution, the solution was placed in a 50° C. oven to accelerate the sol-gel transition. After ripening for 3-5 hours, the solution was electrospun with an applied voltage of 20 kV, a flow rate of 0.03 ml/min, and a tip to collector distance of 4.5 inches. Under these conditions continuous, sub-micron scale fibers were obtained. The electrospun fibers were then heated to 150° C.

for 1 hr to remove residual solvents followed by calcination at 600~800° C. in a tube furnace heated at a rate of 5° C./min for 1~6 hr to produce a silica nanofiber mat.

Example 1(b)

To produce vanadia/silica nanofibers a VOTIP/EtOH solution, containing half of the overall EtOH contents of Example 1(a), was added after vigorous mixing of the TEOS/EtOH and H$_2$O/HCl solutions. The spinning solution contained a 23 mol % V:Si ratio, while a 50 mol % V:Si ratio was used for higher content vanadium fibers. The electrospinning conditions and calcination conditions were the same as that mentioned in Example 1(a).

While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation. The actual scope of the invention is intended to be defined in the following claims.

What is claimed is:

1. An inorganic nanofiber comprising:
   (a) an inorganic matrix material having an external surface, the inorganic matrix material comprising silica; and
   (b) a plurality of metal oxide crystals, the metal oxide crystals positioned within the inorganic matrix material and/or on the external surface.

2. The inorganic nanofiber of claim 1, wherein one or more of the metal oxide crystals is positioned in substantial alignment with a longitudinal axis of the inorganic nanofiber.

3. The inorganic nanofiber of claim 2, wherein between about 25% and about 50% of the crystals are positioned in substantial alignment with the longitudinal axis.

4. The inorganic nanofiber of claim 1, wherein at least a portion of the metal oxide crystals are oriented at an acute angle relative to the external surface.

5. The inorganic nanofiber of claim 1, wherein at least a portion of the metal oxide crystals are oriented randomly in a variety of directions.

6. The inorganic nanofiber of claim 1, wherein between about 8% and about 20% of the external surface comprises the metal oxide crystals.

7. The inorganic nanofiber of claim 1, wherein the metal oxide crystals comprise a metal oxide selected from the group consisting of $V_2O_5$, $VO_2$, $TiO_2$, $Fe_2O_3$, $Fe_3O_4$, $SnO_2$, $ZrO_2$, $BaTiO_3$, $SrTiO_3$ and combinations thereof.

8. The inorganic nanofiber of claim 1, wherein the metal oxide crystals are physically entrapped on the external surface.

9. The inorganic nanofiber of claim 1, wherein the nanofiber is a nanotube.

10. The inorganic nanofiber of claim 1, wherein the nanofiber comprises a plurality of nanofibers that collectively form a nanofiber mat.

11. The inorganic nanofiber of claim 10, wherein the nanofiber mat comprises a specific surface area between about 800.0 m$^2$/g and 1,000.0 m$^2$/g.

12. The inorganic nanofiber of claim 10, wherein the nanofiber mat comprises a plurality of pores.

13. The inorganic nanofiber of claim 1, further comprising amorphous metal oxide physically entrapped within the inorganic matrix material.

14. An inorganic nanofiber comprising: a silica-based matrix material comprising an external surface; and a plurality of metal oxide crystals positioned on the external surface of the inorganic matrix material, with at least about 25% of the metal oxide crystals positioned in substantial alignment with a longitudinal axis of the nanofiber.

15. The inorganic nanofiber of claim 1, wherein the metal oxide crystals do not comprise titania.

16. The inorganic nanofiber of claim 1, further comprising metal oxide precursor.

* * * * *